(12) United States Patent
McMorrow

(10) Patent No.: US 6,402,704 B1
(45) Date of Patent: Jun. 11, 2002

(54) PROTHROMBIN TEST APPARATUS FOR HOME USE

(75) Inventor: Gerald J. McMorrow, Duvall, WA (US)

(73) Assignee: Sonexxus Incorporated, Duvall, WA (US)

( * ) Notice: Subject to any disclaimer, the term of this patent is extended or adjusted under 35 U.S.C. 154(b) by 0 days.

(21) Appl. No.: 09/552,106

(22) Filed: Apr. 18, 2000

(51) Int. Cl.⁷ .................................................. A61B 5/00
(52) U.S. Cl. ........................................ 600/576; 606/181
(58) Field of Search ................................ 600/573, 368, 600/369

(56) References Cited

U.S. PATENT DOCUMENTS

| | | | | |
|---|---|---|---|---|
| 3,879,295 A | * | 4/1975 | Glover et al. ................ | 210/516 |
| 3,912,455 A | * | 10/1975 | Lichtenstein ................. | 23/253 |
| 4,849,340 A | * | 7/1989 | Oberhardt .................... | 435/13 |
| 5,302,348 A | * | 4/1994 | Cusack et al. ................ | 422/73 |
| 6,103,196 A | * | 8/2000 | Yassinzadeh et al. ......... | 422/73 |

* cited by examiner

Primary Examiner—Eric F. Winakur
Assistant Examiner—Pamela L. Wingood

(57) ABSTRACT

The apparatus includes a single-use compartment assembly which includes a reservoir for blood and a needle element by which blood is obtained from the user. A vacuum system is actuated which draws blood through the needle element into the blood reservoir. An ultrasound signal is directed through the reservoir. There is no return ultrasound signal until there is sufficient blood in the reservoir. When the blood reaches a given level, it contacts a clotting agent present in the reservoir to begin the clotting process. The ultrasound signals are transmitted and return until clotting has been completed, as determined by a pre-established increase in the two-way propagation time relative to unclotted blood. The prothrombin time is then calculated and compared with an acceptable range.

17 Claims, 2 Drawing Sheets

PROTHROMBIN TEST APPARATUS FOR HOME USE

TECHNICAL FIELD

This invention relates generally to the determination of blood clotting time, and more specifically concerns an apparatus for conveniently and reliably monitoring blood clotting time, suitable for home use, wherein the blood clotting time is used to monitor dosage levels of anticoagulant medication.

BACKGROUND OF THE INVENTION

It has been estimated that over two million people in the United States are taking anti-coagulant medication, which is used to prevent either a possible first or a repeat stroke incident. The medication dose for a particular individual is selected to produce a prothrombin time (PT), i.e. clotting time, which is high enough to prevent a stroke, but not so high as to substantially prevent clotting, with the accompanying risk of hemorrhage. Dosages to accomplish these objectives vary significantly from patient to patient and even from time to time in the same patient due to dietary and other factors.

Besides the difficulty of maintaining a regular, accurate monitoring of prothrombin times to appropriately balance the blood clotting and hemorrhage risks, it has been established that incorrect levels of medication have significant undesirable side effects in most patients, including various skin effects, diarrhea, fever and nausea. Current medical practice typically prescribes a dose which is significantly below the actual indicated medical level to prevent stroke to avoid the other risks. Regular monitoring, i.e. on a daily basis, however, would likely permit a more appropriate dosage of medication to safeguard against stroke while still avoiding the hemorrhage risk, taking into account effects of diet, etc.

However, regular monitoring has not up to this point been practical due to the cost and inconvenience of repeated visits to a facility where blood is drawn followed by laboratory-testing. Current home-based devices are quite expensive and inconvenient to use on a regular basis, particularly by more elderly patients. One reason for this is the relatively large amount of blood which is required for a prothrombin time analysis by such devices.

Hence, an apparatus suitable for home use which is economical and accurate in establishing prothrombin time, yet requires relatively little blood for each test, would be highly desirable.

SUMMARY OF THE INVENTION

Accordingly, the present invention includes an apparatus for determining prothrombin time, suitable for home use, comprising: a compartment-like assembly which includes therein a reservoir for blood, the reservoir including a blood clotting agent therein; means, such as a needle element, for obtaining blood from a person being tested; means for moving the blood obtained from the person being tested to the blood reservoir; an ultrasound signal device for generating an ultrasound signal and transmitting it through the blood which has been moved into the reservoir when the reservoir contains enough blood to permit two-way propagation of the ultrasound signal but which has not begun to clot and also when the blood has substantially clotted, represented by a known increase in the two-way propagation (transmission) time; and processing means for determining the prothrombin time of the blood from the time it takes for the two-way propagation time to increase by a known amount.

BEST MODE FOR CARRYING OUT THE INVENTION

Figure 1:
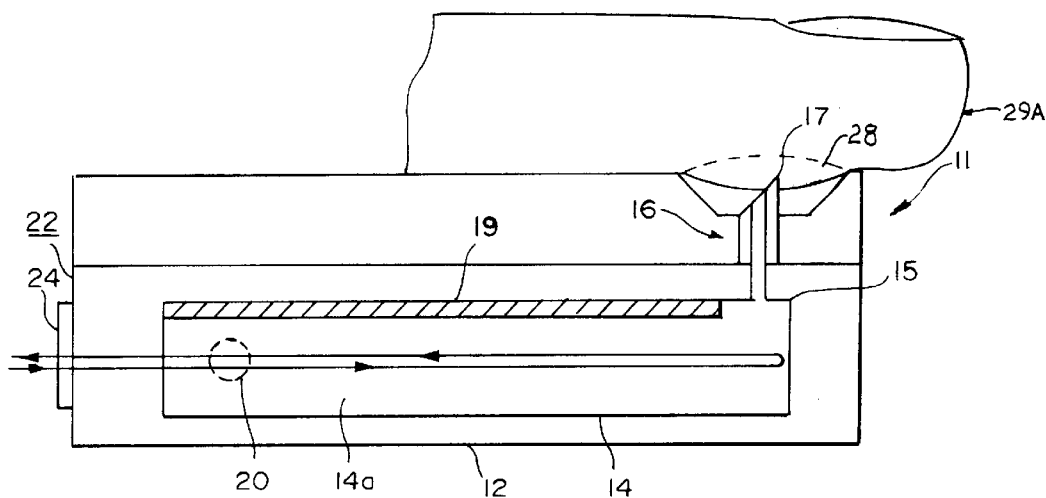
FIG. 1 shows a "consumable" portion of the apparatus of the present invention used for a single prothrombin time test.
Figure 2:
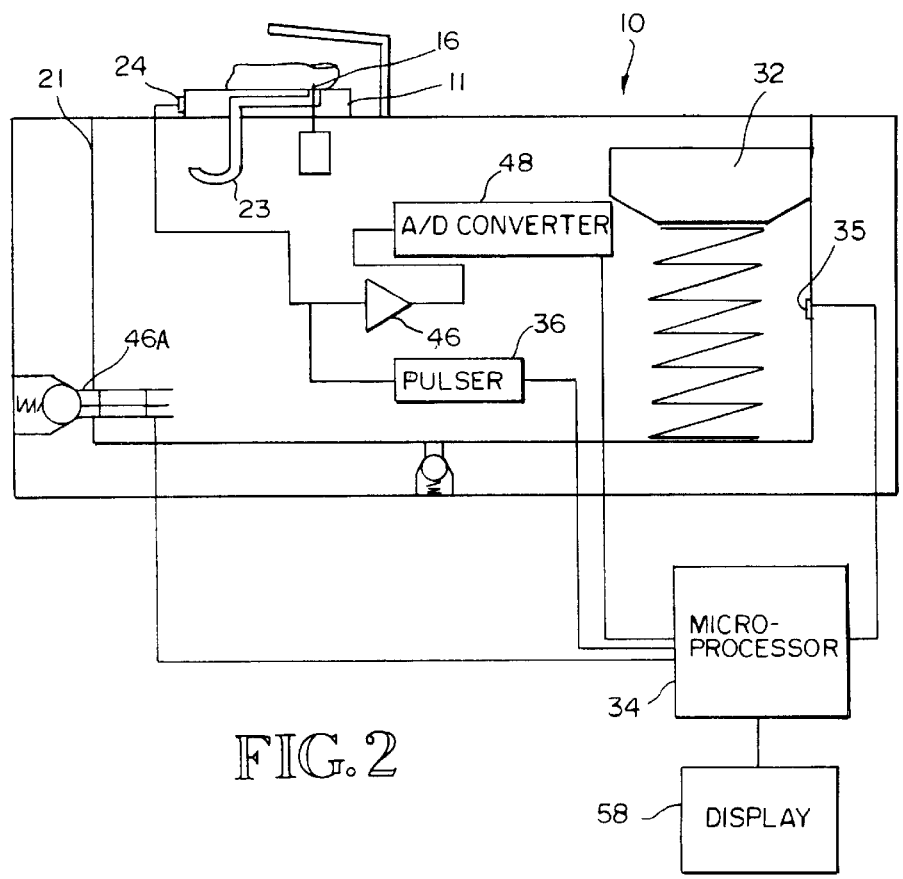
FIG. 2 is a schematic diagram showing the complete home use apparatus of the present invention.

Referring to FIGS. 1 and 2, the prothrombin test apparatus 10 of the present invention is shown. FIG. 2 shows the complete apparatus, while FIG. 1 shows a consumable assembly portion 11 thereof. The consumable assembly portion 11 of the apparatus 10 in the embodiment shown includes a compartment or box 12 which is approximately 25 mm long by 25 mm wide by 6 mm high. Positioned within box 12 is a small, cylindrical plastic blood reservoir 14. At one end 15 of the blood reservoir in the embodiment shown is a small hollow needle 16, which extends through the upper surface of box 12, terminating in a sharp beveled point 17.

In the embodiment shown, blood reservoir 14 is approximately 7.5 mm in length, with a volume of approximately 0.52 cubic centimeters (52 cubic millimeters). The cross-sectional area of the cylinder in the embodiment shown is $7 \times 10^{-6}$ square meters (7 square millimeters). These dimensions are given by way of example only and can be varied. They illustrate the fact that the volume of the blood reservoir, and hence the volume of blood necessary for the test, is quite small. The upper interior surface of the blood reservoir is coated at 19 with a clotting agent, e.g. Thromboplastin, which is well-known in the art. Alternatively, the clotting agent could be coated on a siliconized glass wool element within chamber 14. The compartment or reservoir has a bar code placed thereon, identifying the particular Thromboplastin sensitivity used.

Extending through the longitudinal surface 14a of cylindrical blood reservoir 14 is a vacuum port opening 20. The vacuum port opening 20 connects the interior of reservoir 14 to a vacuum chamber portion 21 of the apparatus 10 shown in FIG. 2, via a vacuum line 23. The vacuum is used to draw blood from the patient into the blood reservoir 14, after the user has punctured a small blood vessel in a finger 29A by placing it against the top of needle 16 with sufficient force. The needle is designed to provide a quick and easy method for the user to provide blood to the reservoir 14.

Prior to the puncturing or pricking of the finger, the tissue of the finger is engorged (area 28 of finger 29A) by vacuum vascularization. This is done so that the blood rapidly exits the puncture point, avoiding "tissue factor" clotting. The first microdrop of blood is moved by the vacuum action beyond chamber 14 so as to remove any "tissue factor" activated blood cells from the testing process. Careful control of vascularization, wound dimensions and removal of "tissue factor" activated blood is important in obtaining accuracy using a very small blood sample.

Figure 3:
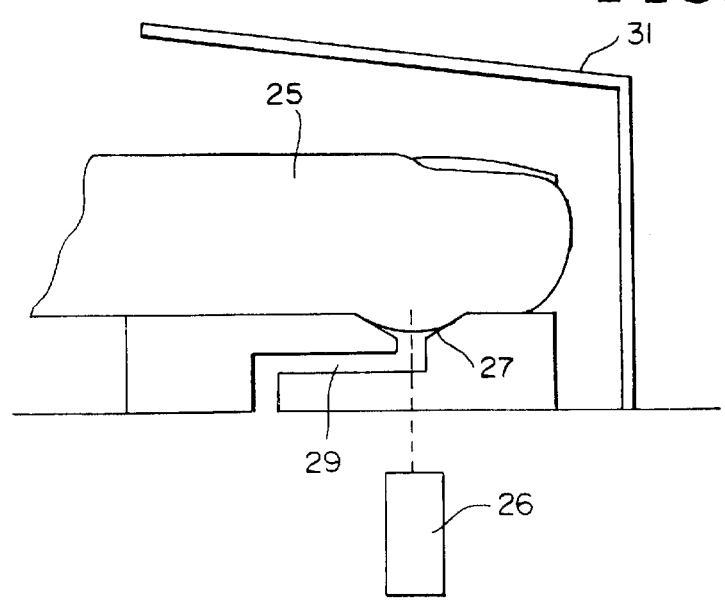
FIG. 3 is a schematic diagram showing an alternative embodiment for a portion of the apparatus of FIG. 2.

FIG. 3 shows an alternative embodiment, in which a finger 25 is placed over an opening 27 at the upper end of a tube 29 which leads to the top of the blood reservoir. A pulsed laser 26 is used to perforate the skin to obtain the blood sample which is moved into the blood chamber through line 29 by vacuum action. A shield 31 is used to protect the patient's eyes from the laser 26.

Referring again to FIGS. 1 and 2, one end surface 22 of box 12 comes into contact with an ultrasound transducer 24 mounted within the apparatus 10, when the consumable assembly portion 11 is positioned within the apparatus. The ultrasound transducer 24, in the embodiment shown, is conventional and is designed to propagate an ultrasound beam down the length of blood reservoir 14.

In the operation of the present invention, explained in more detail below, the prothrombin clotting time is determined to be the time it takes for the two-way ultrasound signal to increase (delay time) by a selected percentage of the two-way signal time for unclotted blood.

As mentioned above, the consumable assembly 11 is positionable within apparatus 10 so that the ultrasound transducer 24 mounted in the apparatus is adjacent one end surface 22 of the consumable assembly 11. The needle assembly 16, which communicates with blood reservoir 14, extends upwardly from compartment 12 and is readily accessible by the user. The consumable assembly 11 becomes part of a manually activated vacuum chamber 21 and the vacuum chamber sealed, when the consumable assembly is properly positioned in the apparatus. Vacuum line 23 extends away from opening 20 in blood reservoir 14 into the vacuum chamber. After the consumable assembly is positioned, a manual plunger 32 is depressed by the user, which initiates the creation of the vacuum in chamber 21. Microprocessor 34 recognizes the action of the plunger 32 and closes on-off switch 35 to the vacuum chamber. The vacuum then begins to draw blood from the patient into the blood reservoir 14 through needle assembly 16. The user has previously positioned a finger on the needle assembly, puncturing a capillary to produce a small blood flow. The vacuum draws the blood from the capillary into the blood reservoir.

The microprocessor 34 reads the bar code on the box/compartment 12, which indicates the calibration and characteristics of the clotting agent in the reservoir. The microprocessor 34 further begins pulsing the ultrasonic transducer 24 via pulsing circuit 36. The ultrasonic transducer 24 will then begin sending ultrasonic signals down the length of the blood reservoir. The propagation time in the embodiment shown is approximately 10 microseconds to cover the length of the reservoir.

Initially, when blood is just beginning to enter the blood reservoir, there is no return signal, because there is no backscatter signal. This signal (no returning portion) will look like FIG. 3A. FIG. 3A shows a transmitted signal 40, but no returning signal.

As the blood reservoir 14 fills with blood, due to vacuum action of chamber 21, there comes a point at which there is sufficient blood to produce a complete ultrasound transmission path, i.e. there is a return signal. At this point, there are both a transmitted signal 42 and a return signal 44, as shown in FIG. 3B. This is for unclotted blood. The theoretical time for the transmission and return of the signal can be calculated, based on the frequency of the ultrasound signal and the length of the blood reservoir. With the dimensions of the reservoir indicated above and a 30 MHz ultrasound signal, the two-way signal time will be approximately 10 microseconds. This is the propagation and return time of the signal for the blood before blood clotting begins, i.e. the unclotted blood signal transmission time.

The returning ultrasound signal is directed to an amplifier 46, the output of which is digitized by an A-D converter 48, the output in turn of which is applied to microprocessor 34 for processing and determination of propagation and return time.

When the ultrasound signal can first traverse the blood reservoir 14 in both directions, i.e. a complete ultrasound path, microprocessor 34 opens vacuum release solenoid 46A. This allows the vacuum in the chamber 21 initiated by action of the plunger 32 to escape, which stops the draw of blood from the patient. The apparatus will then provide an indication, either visual or auditory, that a blood sample has been taken and that they can remove their finger from the needle assembly 16. Only a relatively small amount of blood has been drawn in the process, typically about 0.5–0.7 microliters.

At this point, the reaction between the blood in the reservoir and the Thromboplastin begins, and blood clotting begins. Meanwhile, continued action of pulsing circuit 36 results in a continuing sampling of the two-way ultrasound propagation time every millisecond with a precision of +10 nanoseconds.

Figure 4A:
FIG. 4 is a simple signal diagram illustrating the determination of prothrombin time by the apparatus of FIG. 2.
Figure 4B:
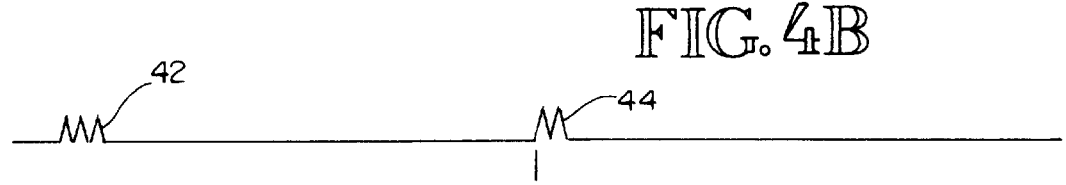
Figure 4C:
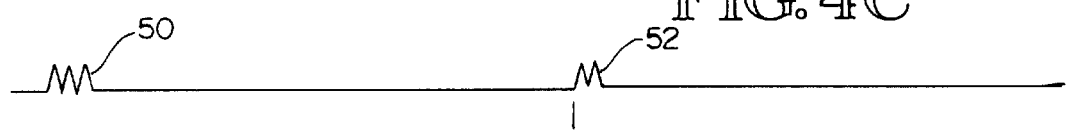

When the arrival time of the returning signal changes by a predetermined percentage, approximately 1%, from 10 microseconds to 10.1 microseconds with a 10 nanosecond resolution, which is relatively easy to distinguish, the blood has completed the clotting action. This is shown by waveforms 50 and 52 in FIG. 4C. The prothrombin time, i.e. the time it takes for the blood to clot, is determined by the time it takes for the two-way ultrasound time to increase by 0.1 microseconds (the difference between time for unclotted blood and the time when the blood is clotted).

Again, in summary of operation, an ultrasound signal is propagated the length of the blood reservoir every millisecond and returns. The ultrasound signal begins to return when unclotted blood fills the blood reservoir. Ultrasound transmission and return continues until the two-way time for the signal has increased by a preselected amount, which in the embodiment shown, is approximately 0.1 microseconds. For the embodiment described, it is known that clotting has occurred when the two-way propagation time increases by 0.1 microseconds relative to unclotted blood. The microprocessor 34 determines the prothrombin (clotting) time it takes for the waveform of FIG. 4B to change to the waveform of FIG. 4C.

After the prothrombin time has been calculated, it can be displayed in terms of being in or out of an acceptable range on a display means 58 in or connected to the apparatus 10. A record of all the prothrombin time measurements can in addition be maintained locally in the apparatus (the microprocessor). Further, information concerning each prothrombin time measurement, including the exact time of each measurement, the instrument identification number and the prothrombin time, can be transmitted to a central server via the internet. That information will provide the physician a long-term record of the patient's prothrombin time. An immediate alert, through means such as E-mail, a pager or automated phone message can be provided if the information indicates that the patient is out of range, or if the patient has not been measuring on a timely basis. Hence, patient compliance with the measurement routine can be monitored, as well as prothrombin time.

Accordingly, the present invention is an apparatus which can be used at home and is relatively simple and straightforward to operate. Its advantages are that it requires only a small amount of blood, and is relatively easy to use.

Although a preferred embodiment of the invention has been disclosed here for purposes of illustration, it should be understood that various changes, modifications and substitutions may be incorporated without departing from the spirit of the invention, which is defined by the claims which follow.

What is claimed is:

1. An apparatus for determining prothrombin time, suitable for home use, comprising:

a compartment assembly which includes a reservoir for blood, the reservoir including a blood clotting agent;

means for obtaining blood from a person being tested;

means for moving said blood into the reservoir;

an ultrasound signal device for generating an ultrasound signal and transmitting it through the blood in the reservoir both at a time when the reservoir contains blood which has not yet begun to clot but in a quantity sufficient to sustain two-way transmission of the ultrasound signal and when the blood has substantially clotted, represented by a known increase in the two-way transmission time; and processing means for determining the prothrombin time of the blood from the time it takes for the two-way transmission time to increase by a known amount.

2. An apparatus of claim 1, wherein the means for obtaining blood is a needle element which communicates with the reservoir.

3. An apparatus of claim 1, wherein the means for obtaining blood is a laser device which perforates the skin of the person being tested sufficiently to obtain blood therefrom.

4. An apparatus of claim 1, including means for comparing said prothrombin time to an established range and for providing an alarm indication when the prothrombin time is outside said established range.

5. An apparatus of claim 2, wherein said needle element is configured and positioned such that a patient can readily produce a puncture contact between said needle element and said blood vessel by applying pressure on a finger against the needle.

6. An apparatus of claim 1, wherein said blood drawing means is a vacuum chamber which when activated draws blood into the blood reservoir.

7. An apparatus of claim 2, wherein the compartment assembly is configured as a single unit and is arranged for a single use, and wherein the compartment assembly is readily removable and insertable relative to the remainder of the apparatus.

8. An apparatus of claim 6, including a vacuum release member in the vacuum chamber which is activated to terminate the drawing of blood when sufficient blood is in the reservoir to sustain a two-way propagation of the ultrasound signal.

9. An apparatus of claim 1, including an ultrasound transducer which is positioned in the vicinity of one end of the compartment assembly, which in operation produces ultrasound signals which propagate along the length of the reservoir and back.

10. An apparatus of claim 6, wherein the vacuum chamber is manually actuated by the user to initiate operation of the apparatus.

11. An apparatus of claim 1, wherein the frequency of the ultrasound signal is sufficiently high and the blood reservoir is so configured that the difference in time of propagation and return of the ultrasound signal between non-clotted blood and clotted blood is readily ascertainable.

12. An apparatus of claim 11, wherein said time difference is approximately 0.1 microseconds.

13. An apparatus of claim 1, wherein said compartment includes an identification of the clotting agent therein, and wherein the apparatus includes means for reading the identification and transmitting that information to the processing means.

14. An apparatus of claim 13, wherein the identification is a bar code.

15. An apparatus of claim 1, including a vacuum member for engorging the tissue where blood is to be obtained.

16. A single use compartment assembly attached to an apparatus for determining prothrombin time, comprising:

a compartment adapted for removable attachment to said apparatus;

a blood reservoir positioned within the compartment, the reservoir containing a blood clotting agent; and a needle assembly, communicating with said reservoir for permitting blood obtained from a blood vessel of a person being tested to be moved into said reservoir, wherein the person being tested places a finger on the needle element to produce a puncture contact with a blood vessel and wherein the compartment assembly and the needle assembly are configured as a single unit and are arranged for a single use, and wherein the compartment assembly is readily removable and insertable relative to the apparatus.

17. An apparatus of claim 16, wherein said needle element is configured and positioned such that a patient can readily produce a puncture contact between said needle element and said blood vessel by applying pressure on a finger against the needle element.

* * * * *